US009925647B2

(12) United States Patent
Lafond et al.

(10) Patent No.: US 9,925,647 B2
(45) Date of Patent: Mar. 27, 2018

(54) DEVICE FOR HOLDING A SAMPLING SPONGE

(75) Inventors: Danielle Lafond, Mont Saint-Hilaire (CA); May L. Scally, St. Mathias sur Richelieu (CA); Louis Therrien, Sainte-Julie (CA); Alain Chevigny, Val-Morin (CA)

(73) Assignee: LABPLAS INC., Sainte-Julie (CA)

( * ) Notice: Subject to any disclaimer, the term of this patent is extended or adjusted under 35 U.S.C. 154(b) by 0 days.

(21) Appl. No.: 13/294,168

(22) Filed: Nov. 10, 2011

(65) Prior Publication Data
US 2013/0118275 A1  May 16, 2013

(51) Int. Cl.
G01N 1/04 (2006.01)
B25B 9/02 (2006.01)
(Continued)

(52) U.S. Cl.
CPC ............. B25B 9/02 (2013.01); B25B 9/00 (2013.01); G01N 1/02 (2013.01); G01N 2001/028 (2013.01)

(58) Field of Classification Search
CPC ............. G01N 1/02; G01N 2001/028; G01N 2001/007; A46B 2200/304; A46B 5/0095; A46B 9/005; A46B 7/04; A47K 11/10; B25B 9/00; B25B 9/02; A47L 13/46; A47L 13/20
(Continued)

(56) References Cited

U.S. PATENT DOCUMENTS 902,726 A  11/1908  Greer
938,421 A  10/1909  Hakins
(Continued)

FOREIGN PATENT DOCUMENTS

CA  2428865  11/2003
CA  2757811  5/2013
(Continued)

OTHER PUBLICATIONS

English Abstract of CA142081(S), "Handle for holding a sampling sponge", published on Apr. 23, 2014.
(Continued)

Primary Examiner — Helen Kwok
Assistant Examiner — Nashmiya Fayyaz
(74) Attorney, Agent, or Firm — Bereskin & Parr LLP/S.E.N.C.R.L., s.r.l.

(57) ABSTRACT

A device for swabbing a surface and collecting a substance therefrom comprises a handle and a sponge releasably mounted to the handle. The handle includes at least one gripping member adapted to engage the sponge and retain the sponge mounted to the handle in a first position of the gripping member, the gripping member being adapted upon pressure exerted on an actuator to move the gripping member to a sponge-release position thereof for releasing the sponge from the handle. Typically, there are provided two opposed gripping members, wherein the pressure is exerted by a user's fingers on each gripping member and towards one another. The gripping members are actuated to the sponge-release position without requiring that the user substantially moves his/her hand and fingers longitudinally along the handle.

15 Claims, 12 Drawing Sheets

(51) Int. Cl.
*B25B 9/00* (2006.01)
*G01N 1/02* (2006.01)

(58) Field of Classification Search
USPC .......................... 73/864.71; 15/209.1, 210.1
See application file for complete search history.

(56) References Cited

U.S. PATENT DOCUMENTS

| | | |
|---|---|---|
| 1,376,779 A | 5/1921 | Penrod |
| 1,592,950 A | 7/1926 | McClain |
| 1,631,791 A | 6/1927 | Buckley |
| 1,637,595 A * | 8/1927 | Sturgis .................... 15/147.2 |
| 2,214,984 A | 9/1940 | Bachmann |
| D155,308 S | 9/1949 | Morrison |
| 2,590,614 A | 3/1952 | Hawkins, Sr. |
| 2,731,696 A | 1/1956 | Sutton |
| 2,762,070 A | 9/1956 | Tingley |
| 2,936,475 A | 5/1960 | Johns |
| 3,058,139 A | 10/1962 | Dryden |
| 3,115,360 A | 12/1963 | Witkoff |
| 3,137,880 A | 6/1964 | Kukit et al. |
| 3,220,040 A | 11/1965 | Knaebe |
| 3,589,369 A | 6/1971 | Alksnis |
| 3,809,094 A | 5/1974 | Cook |
| D243,060 S | 1/1977 | Graham et al. |
| 4,175,439 A * | 11/1979 | Laker .................. A61B 10/007 |
| | | 422/944 |
| D263,512 S | 3/1982 | Kawada |
| 4,401,130 A | 8/1983 | Halford et al. |
| 4,934,011 A | 6/1990 | Haug |
| 4,950,281 A | 8/1990 | Kirsch et al. |
| 5,047,046 A | 9/1991 | Bodoia |
| 5,084,931 A | 2/1992 | Kühlcke |
| D330,444 S | 10/1992 | Wall et al. |
| D340,768 S | 10/1993 | Jabour |
| 5,261,918 A | 11/1993 | Phillips et al. |
| D350,272 S | 9/1994 | Kahn et al. |
| 5,435,037 A * | 7/1995 | Ledingham ................ 15/168 |
| 5,520,704 A | 5/1996 | Castro et al. |
| D374,110 S | 9/1996 | Hull et al. |
| 5,564,829 A | 10/1996 | Lafond |
| 5,823,592 A * | 10/1998 | Kalidindi .................. 73/864.71 |
| D417,320 S | 11/1999 | Nunez |
| D422,148 S | 4/2000 | King et al. |
| 6,142,661 A | 11/2000 | Lafond |
| 6,267,498 B1 | 7/2001 | Lafond et al. |
| D449,910 S | 10/2001 | Hendricks |
| 6,383,804 B1 | 5/2002 | Ward, Jr. et al. |
| D461,027 S | 7/2002 | Gardner |
| 6,575,202 B2 | 6/2003 | Lafond |
| 6,611,986 B1 * | 9/2003 | Seals ........................ 15/210.1 |
| 6,616,683 B1 | 9/2003 | Toth et al. |
| 6,827,482 B2 | 12/2004 | Lafond et al. |
| D502,324 S | 3/2005 | Conway et al. |
| D503,229 S | 3/2005 | Davis et al. |
| D511,032 S | 10/2005 | Roberts |
| D517,874 S | 3/2006 | Heck |
| 7,014,231 B1 | 3/2006 | Callen |
| D518,597 S | 4/2006 | Sommers |
| 7,316,046 B2 * | 1/2008 | Michaels et al. ............ 15/210.1 |
| 7,386,910 B2 * | 6/2008 | Minkler et al. ............. 15/145 |
| D587,412 S | 2/2009 | Oka |
| 7,530,138 B1 * | 5/2009 | Platt ............................ 15/210.1 |
| 7,665,177 B2 | 2/2010 | Forrest |
| D617,061 S | 6/2010 | Su |
| 7,814,608 B1 | 10/2010 | Catello |
| D676,732 S | 2/2013 | Lafond et al. |
| D706,947 S | 6/2014 | Hooper |
| 8,740,274 B1 | 6/2014 | Dugas |
| 8,875,337 B2 * | 11/2014 | Tacoma ..................... 15/209.1 |
| D734,901 S | 7/2015 | Milan |
| 9,072,280 B1 | 7/2015 | Ramoutar |
| D772,680 S | 11/2016 | Lafond et al. |
| 2002/0197738 A1 * | 12/2002 | Matsumoto ........ A61B 10/0051 |
| | | 436/518 |
| 2003/0155783 A1 | 8/2003 | Hsu |
| 2005/0010132 A1 * | 1/2005 | Pestes et al. .................. 600/572 |
| 2009/0139351 A1 * | 6/2009 | Reichmuth et al. ....... 73/864.11 |
| 2009/0255078 A1 * | 10/2009 | Wada et al. ................. 15/209.1 |
| 2011/0004122 A1 * | 1/2011 | Sangha .............. A61B 10/0045 |
| | | 600/572 |
| 2011/0296639 A1 * | 12/2011 | Strauss ......................... 15/145 |
| 2012/0310113 A1 * | 12/2012 | Giddings ........... A61B 10/0051 |
| | | 600/570 |
| 2013/0017134 A1 | 1/2013 | Scally et al. |
| 2013/0118275 A1 | 5/2013 | Lafond et al. |
| 2015/0203323 A1 | 7/2015 | Scally et al. |
| 2015/0353312 A1 | 12/2015 | Brouillette et al. |

FOREIGN PATENT DOCUMENTS

| | | |
|---|---|---|
| CA | 2839218 | 7/2015 |
| WO | 2012040810 | 4/2012 |
| WO | 2017015740 | 2/2017 |

OTHER PUBLICATIONS

English Abstract of CA147081(S), "Handle for holding a sampling sponge", published on Apr. 23, 2014.
English Abstract of CA154729(S), "Device for supporting a sampling bag", published on Jul. 22, 2016.
English Abstract of CA155855(S), "Bag dispenser", published on Oct. 26, 2015.
English Abstract of CA162736(S), "Device for supporting a sampling bag", published on Jul. 22, 2016.

* cited by examiner

DEVICE FOR HOLDING A SAMPLING SPONGE

FIELD OF THE INVENTION

The present invention relates to the sponges and, more particularly, to sponges for swabbing surfaces for subsequently determining the presence of pathogens.

BACKGROUND OF THE INVENTION

It is well known that the food industry is subjected to guidelines and protocols of regulatory organizations such as the FDA in the United States and Health Canada in Canada, and certified food safety, processes such as Hazard Analysis Critical Control Point (HACCP). Similar protocols, to varying degrees, are in place around the globe, including Europe, Asia, Africa, etc.

These norms dictate that, amongst other things, food handling surfaces, containers and equipment must be sampled in order to detect the potential presence of hazardous pathogens. The food industry uses various versions of sponge products in order to perform surface swabs and sampling for pathogen detection.

There are versions of such sponges that are mounted on a handle in order to facilitate swabbing of hard-to-reach areas, such as the insides of food processing machinery, work area nooks and crannies, animal carcasses, etc., which would be more difficult to reach if one was using a simple handheld sponge.

A few versions of mounted sampling sponges exist on the market today and each has its drawbacks in terms of practicality and user friendliness.

Generally, a 1.5 in. by 3 in. sponge, usually pre-moistened with a neutralizing solution, is mounted, for instance by adherence, to a plastic handle. This device comes in a sterile sampling bag and is also available with sterile gloves. The user, wearing gloves, opens the sterile sampling bag and extracts the handle with its mounted sponge. The sponge is then used to swab a predetermined area of the surface to be tested. Once swabbing is completed, the sponge (which in fact has collected the specimen of surface contaminants) is removed from the handle, put back into the sterile sampling bag, which is closed and then forwarded to a lab, for incubation and analysis.

One known product consists of a simple and relatively flexible polyethylene handle. The moistened sponge is heat welded to and adheres to the top of the handle in a permanent fashion.

Once the user has swabbed the test surface, he then snaps the plastic handle and inserts the sponge, still adhered to the broken piece of handle, into the sterile sampling bag, to then be transported to a lab for analysis. This action requires the use of both hands, making it awkward. A third hand would be required to keep the receiving sample bag open and stable.

Furthermore, the piece of rigid plastic in the sampling bag is awkward for handling in the lab, increases the risk of a punctured bag and is generally cumbersome.

Another product has a sponge-holding handle assembly that includes two specific components: 1) an elongated handle, which is made of slightly flexible mix of HDPE and LDPE (High Density and Low Density polyethylene) and which has end prongs that the sponge is folded onto; and 2) a second rigid component that slides up and down along the elongated handle, and when the second rigid component is in its upper or distal position, it retains the sponge in place oat the end of the elongated handle, whereas, when the second rigid component is pulled to its lower or proximal position, it allows the sponge to be released from the elongated handle.

This version is cumbersome in that two free hands are also requires to operate the release of the sponge. Furthermore, this version is quite large, requires two separated molded plastic parts and is thus significantly expensive to manufacture, and thus possibly cost prohibitive.

Therefore, there is a need in the art for an improved sampling sponge of the type releasably mounted on a handle.

SUMMARY OF THE INVENTION

It is therefore an aim of the present invention to provide a novel sampling device including a sponge.

Therefore, in accordance with the present invention, there is provided a device for swabbing a surface and collecting a substance therefrom, comprising a handle and a collecting member releasably mounted to the handle, the handle including at least one gripping member adapted to engage the collecting member and retain the collecting member mounted to the handle in a first position of the gripping member, the gripping member being adapted upon pressure exerted on an actuator to move the gripping member to a collecting member-release position thereof for releasing the collecting member from the handle.

Also in accordance with the present invention, there is provided a handle for use with a collecting member adapted to swab a surface and collecting a substance therefrom, the handle being adapted to releasably hold a collecting member thereto, the handle including at least one gripping member adapted to engage the collecting member and retain the collecting member mounted to the handle in a first position of the gripping member, the gripping member being adapted upon pressure exerted on an actuator to move the gripping member to a collecting member-release position thereof for releasing the collecting member from the handle.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

Reference will now be made to the accompanying drawings, showing by way of illustration an illustrative embodiment of the present invention, and in which.

DESCRIPTION OF ILLUSTRATIVE EMBODIMENTS OF THE INVENTION

Figure 4:
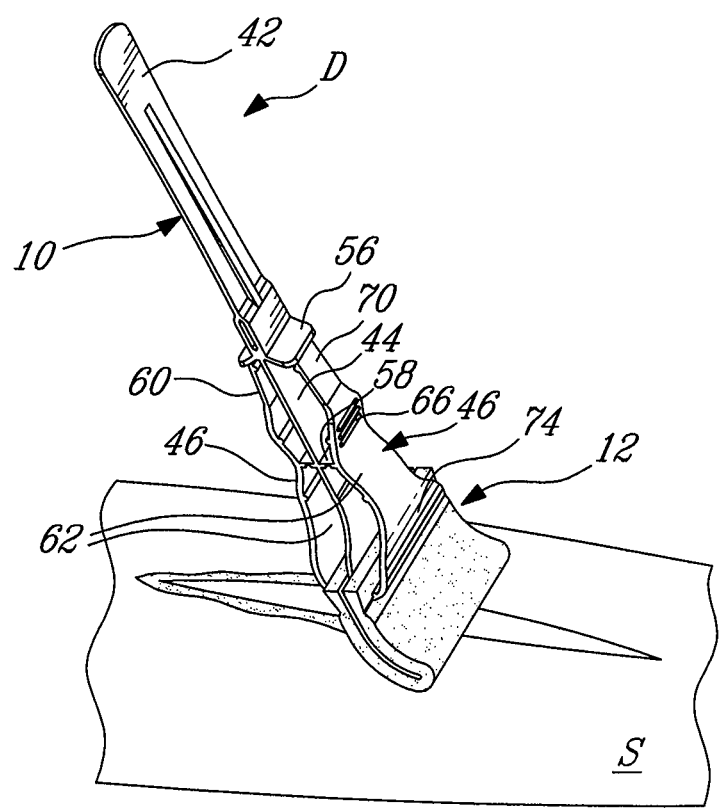
FIG. 4 is a perspective view of the sampling device of FIG. 1 shown in use as a sponge thereof is being swabbed along a surface.
Figure 5A:
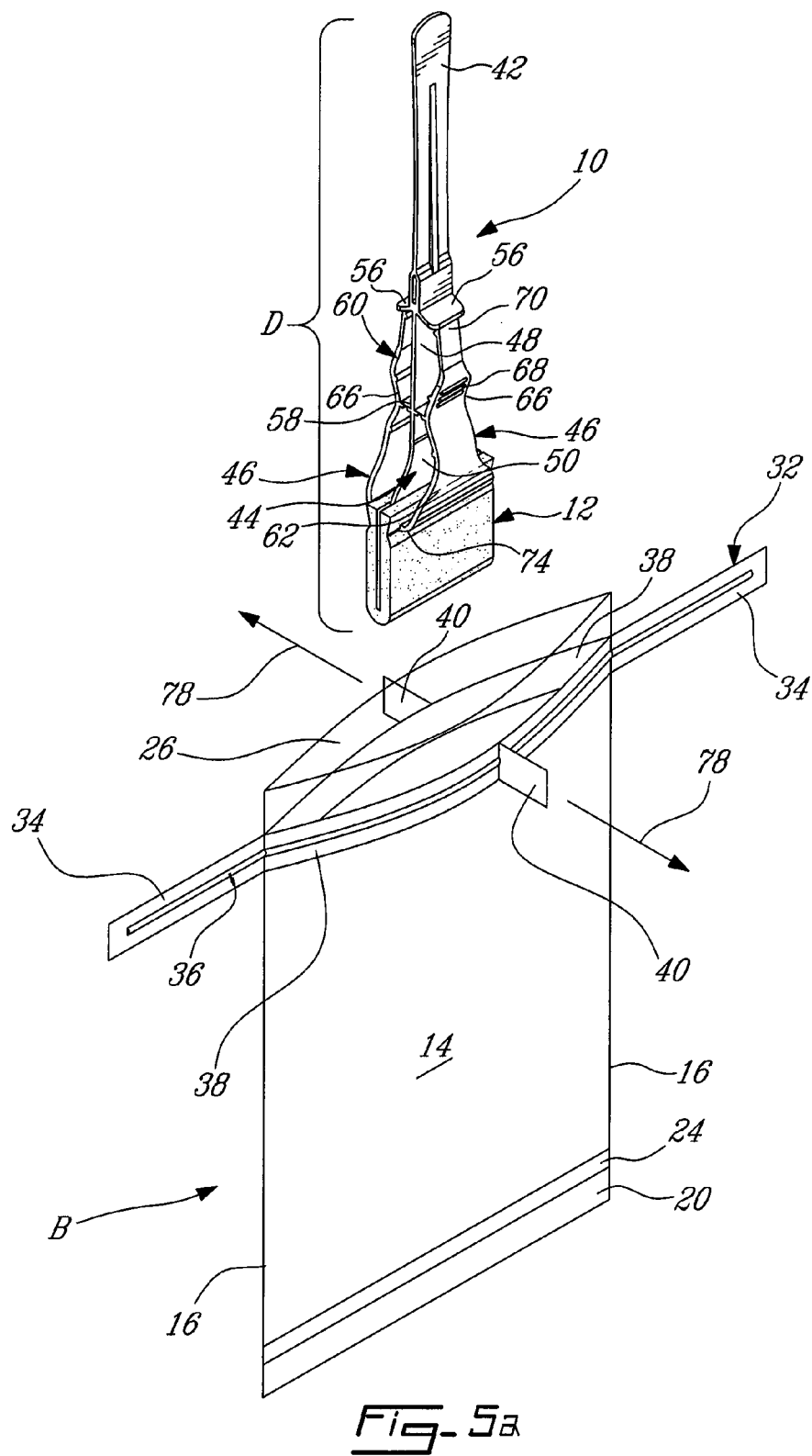
FIGS. 5a to 5d are sequential perspective views showing the swabbed sponge of the sampling device being positioned and sealed in the sampling bag.
Figure 5B:
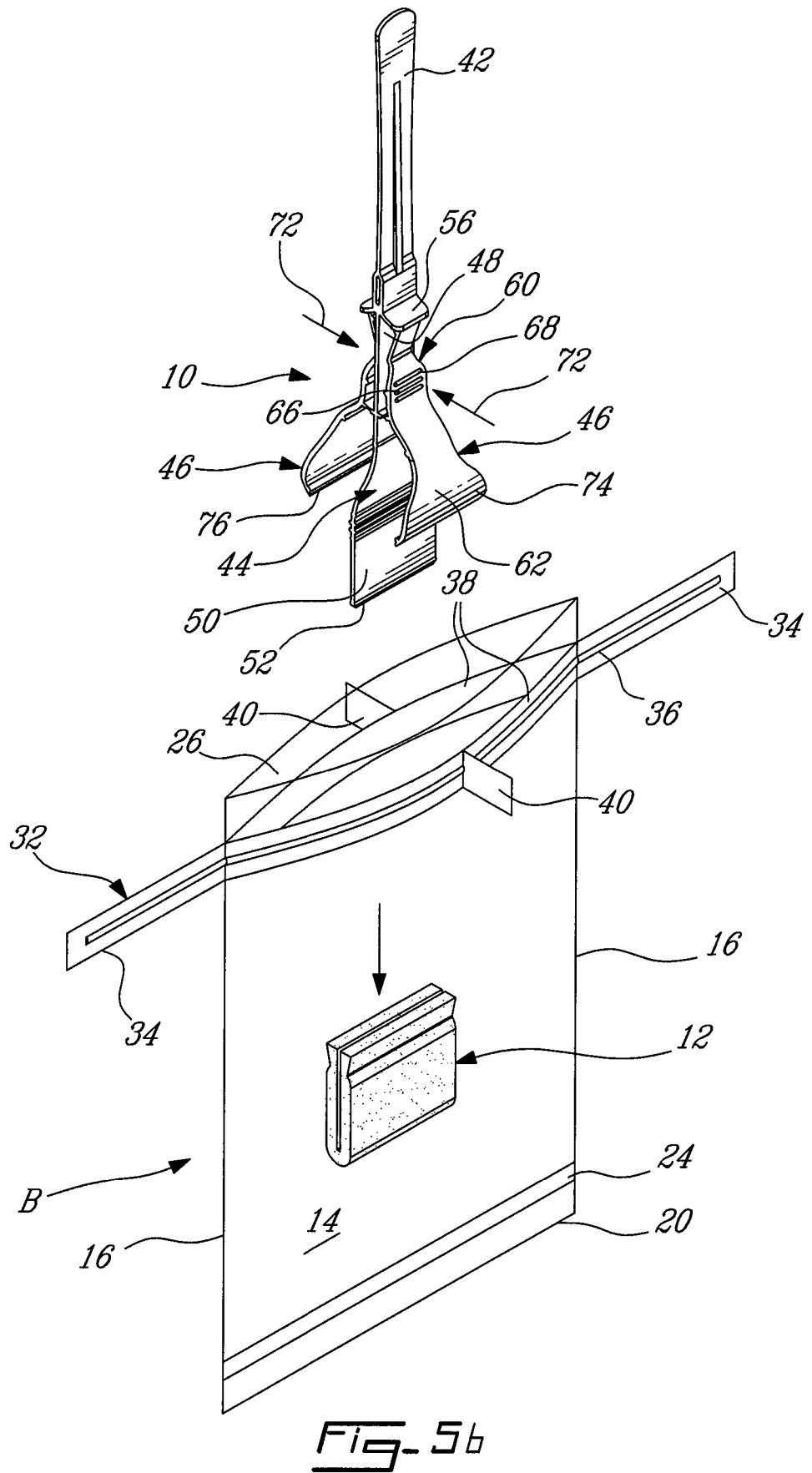

With reference to the drawings, there will now be described a sampling device D, which includes a handle 10 and a sponge 12 releasably attached to the handle 10, as will be described in details hereinafter. A sterile sampling bag B is also provided to firstly house sterilely the sampling device D (as seen in FIG. 1) and to secondly contain the sponge 12 after it has been swabbed and deposited in the bag B (as seen in FIGS. 4 to 5*d*).

The sampling device D is considered to obviate some drawbacks of known products being used for the same purpose.

The present sampling device D has a cost effective design and can be operated (i.e. release of the sponge 12 in the bag B) using one hand. The sampling device D does not involve a residual of broken plastic and therefore meets both industry and regulatory requirements.

Figure 1:
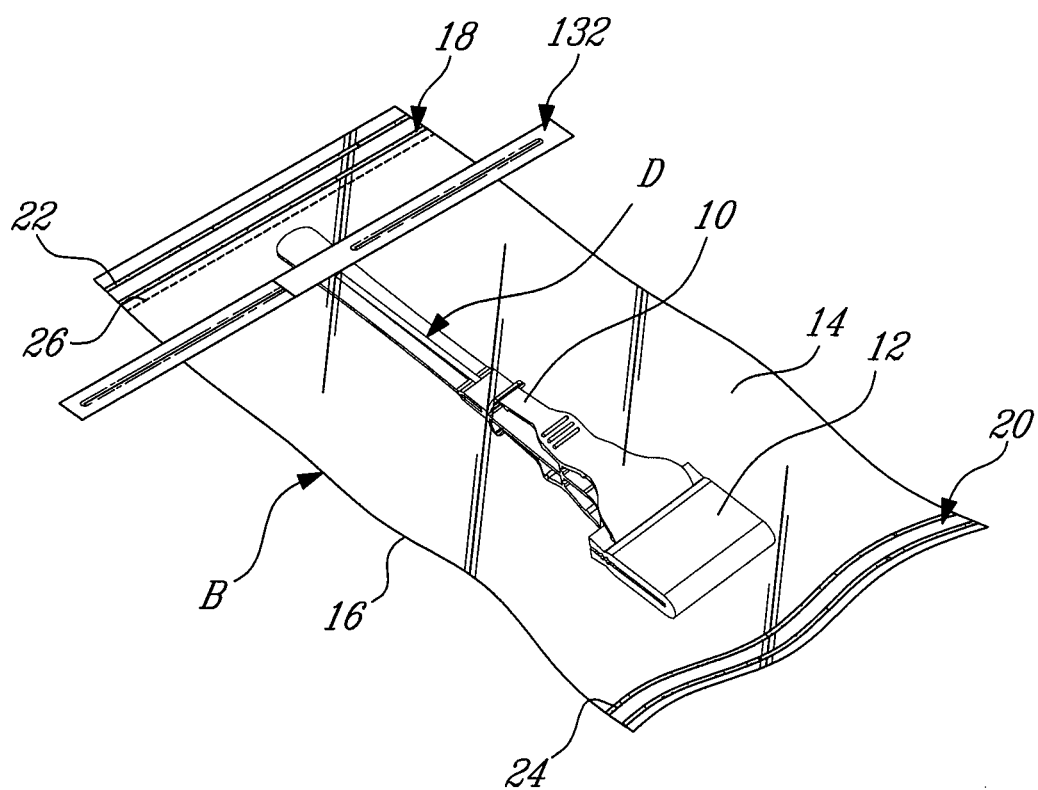
FIG. 1 is a schematic perspective view of a sampling device in accordance with the present invention, shown prior to use in a sealed sampling bag.
Figure 2:
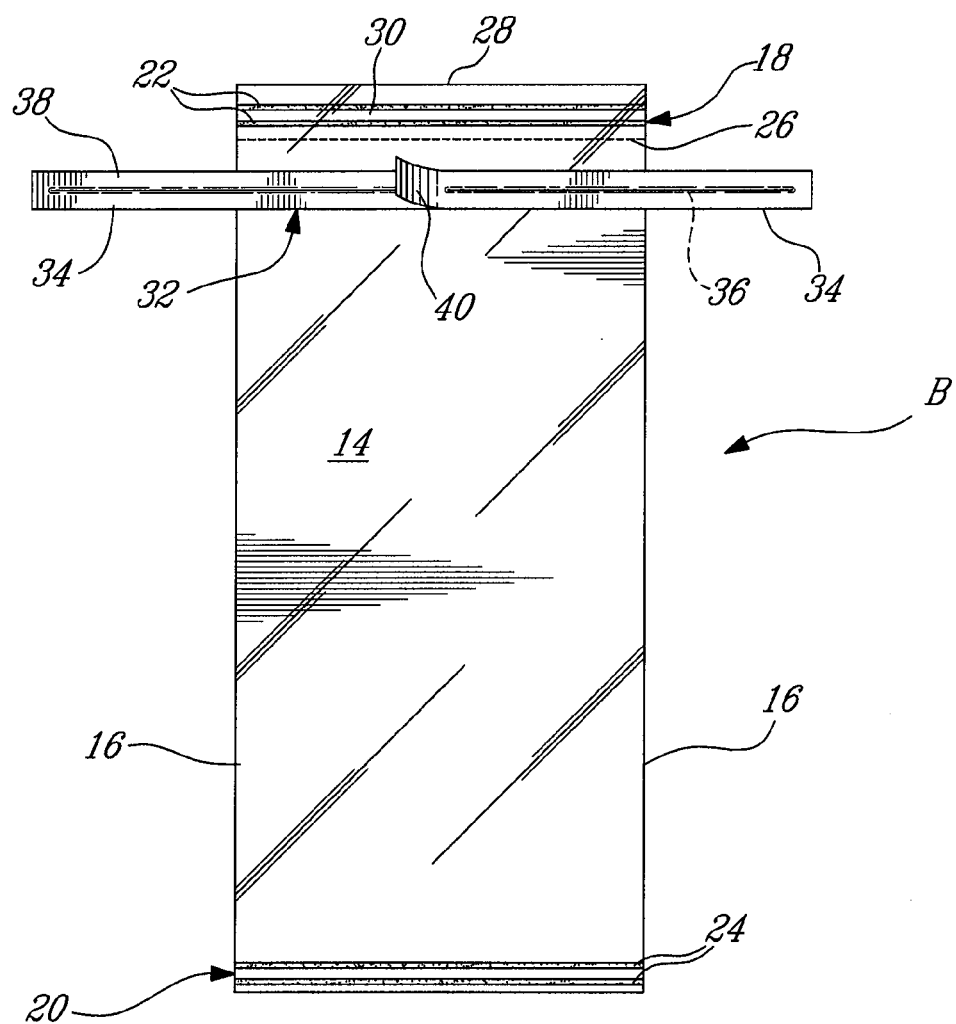
FIG. 2 is a front view of a sampling bag similar to that of FIG. 1 and in a state thereof prior to use, the sampling device not being herein shown.
Figure 3:
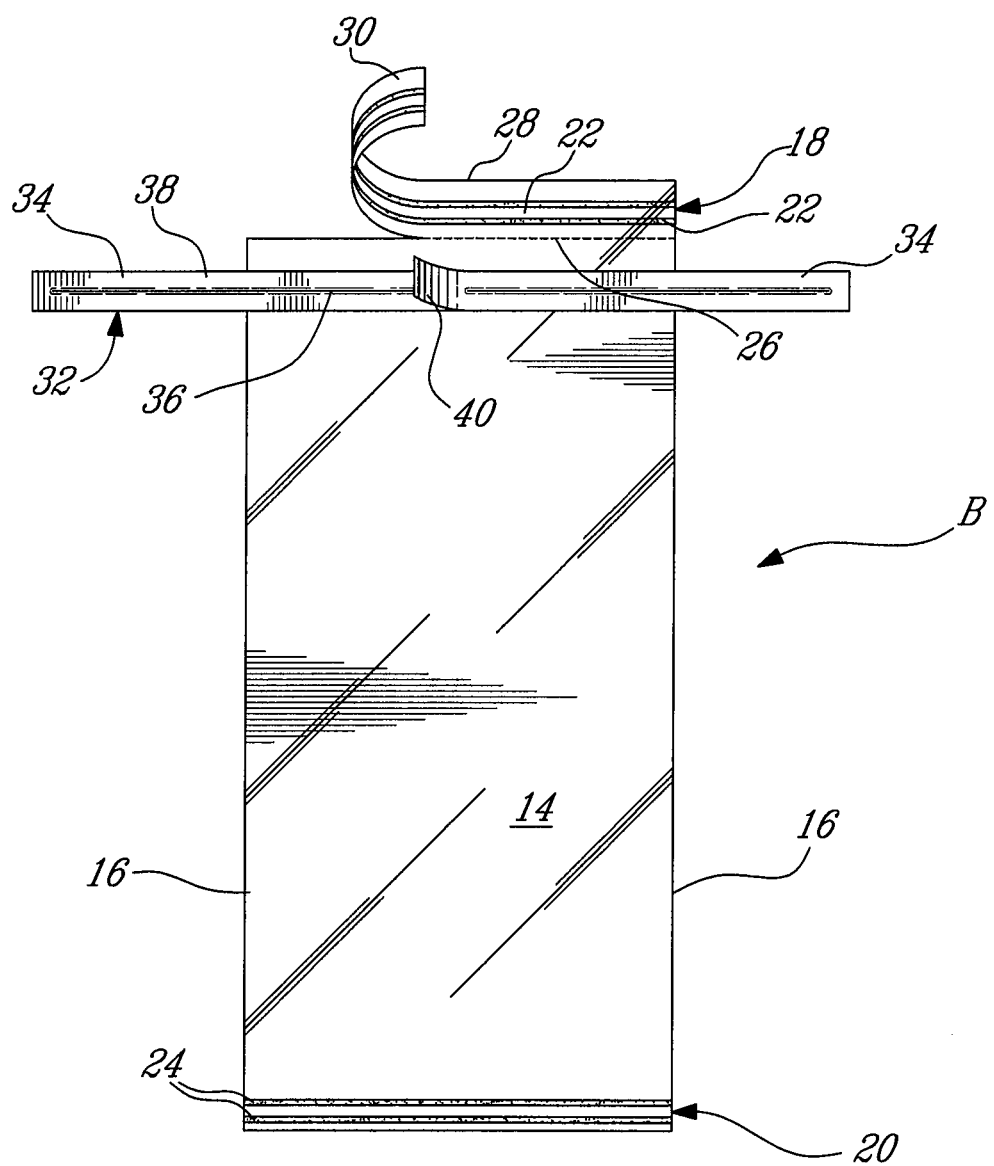
FIG. 3 is a front view of the sampling bag FIG. 2 and shown in the process of being opened, the sampling device not being herein shown.

With reference mainly to FIGS. 1 to 3, the sample bag B is a disposable, sterile and typically made of plastic bag. In an exemplary construction, the bag B comprises identical front and rear sheets 14 integrally joined at the side edges 16 thereof, generally as a result of the bag B being made from a tube, and having opposite upper and lower ends 18 and 20, respectively. The two sheets 14 are joined in a tight sealed manner at the upper end 18 of the bag B by a heat seal 22, with two parallel and spaced such heat seals 22 being herein shown. Similarly, the two sheets 14 are sealingly joined at the lower end 20 of the bag B by a lower heat seal 24, also herein embodied by a pair of heat seals 24 which ensure sterility and leakproofness of the bag B.

A tear off line 26 is punctured through both sheets 14 across the upper end 18 of the bag B and lower than the upper heat seals 22 such that the upper heat seals 22 extend substantially parallelly between the tear off line 26 and an upper edge 28 of the bag B. Therefore, there is a tear off strip 30 defined at the upper end 18 of the bag B which when detached from the remainder of the bag B (in a manner initiated and shown in FIG. 3), reveals an open mouth at the tear off line 26 of the bag B through which the sponge 12 (once swabbed) can be inserted into the bag B so as to be stored in the bag B. The tear off strip 30 preserves the sterility of the bag B until its manipulation.

The bag B further includes near the mouth thereof, that is just below the tear off line 26, a closure member 32 which is mounted transversely across the bag B with ends 34 (acting as pull-tabs) of the closure member 32 extending past the side edges 16 of the bag B. The closure member 32, in a known manner, includes a pair of metal strips or wires 36 (one disposed outwardly on each of the front and rear sheets 14) and a pair of adhesive tapes 38 disposed outwardly over the metal wires 36 to attach the metal wires 36 to the front and rear sheets 14 of the bag B with the tapes 38 adhering to the bag B inwardly of the side edges 16 thereof while adhering together outwardly of the side edges 16. The closure member 32 allows for the bag B to be repeatedly opened and closed without risk of loss of contents or contamination.

Therefore, once the tear off strip 30 has been removed from the bag B, the bag B may be opened by spreading side pull-tabs 40 (one such pull-tab extending outwardly from the middle of each adhesive tape 38) thereby avoiding contamination of the inside of the bag B. Then, the sampling device D (which was sterilely housed in the bag B as seen in FIG. 1) can be removed from the bag B so that the sponge 12 thereof can be swabbed on a surface to be tested and thereafter dropped into the bag B, as it will be described in more details hereinafter.

The bag B is then closed using the closure member 32. More particularly, the longitudinal ends 34 of the closure member 32 (i.e. its portions extending outwardly beyond the side edges 16 of the bag B) are then pulled away so as to draw the front and rear sheets 14 together opposite the closure member 32 thereby substantially closing the upper mouth of the bag B. After, pressure can be applied on the outside of the bag B to remove trapped air. The closure member 32 is then rolled down along the bag, for instance four (4) times over, and the longitudinal ends 34 of the closure member 32 are folded inwardly, at the side edges 16 of the bag B, over either the front and rear sheets 14 to prevent the "unrolling" of the closed upper end of the bag B. This safely and effectively encloses the swabbed sponge 12 in the plastic bag B.

Now turning to the sampling device D, the handle 10 and sponge 12 thereof will be further described, and reference is made mainly to FIGS. 6 to 9.

Figure 10:
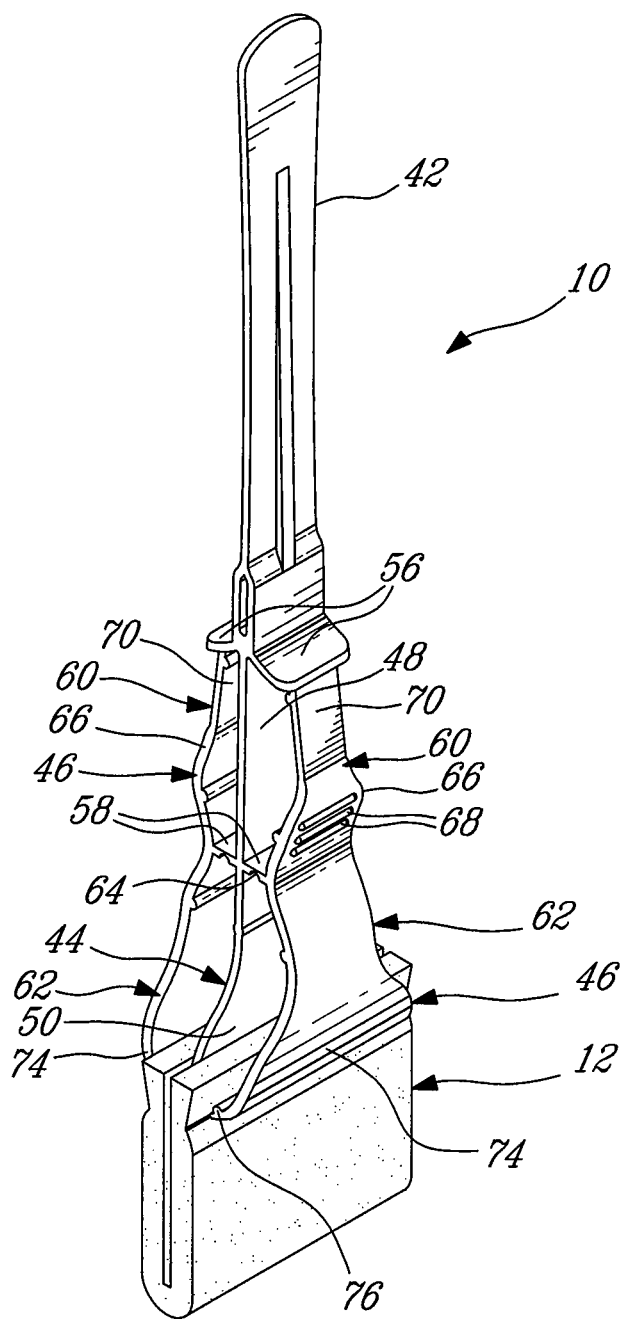
FIG. 10 is a perspective view of the sponge mounted to the handle of the sampling device.

The handle 10 is typically made of plastic, in one piece. The handle 10 includes a hand grip 42, a longitudinal web 44 extending distally from the hand grip 42, and a pair of opposed gripping members 46. The hand grip 42 can be flexible so as to conform to the user's hand when he/she is holding the sampling device D threat. The web 44 includes a proximal portion 48 located between the gripping members 46, and a wider distal portion 50 mostly extending distally from the gripping members 46. As seen in FIG. 10, the sponge 12 is folded at a free edge 52 of the distal portion 50 and then extends on both sides of the distal portion 50 of the web 44 (and the sponge 12 is held thereto via the gripping members 46, as described hereinafter). Transversal ribs 54 are defined on both sides of the distal portion 50 of the web 44 (there being herein 4 ribs per web side) for engaging proximal ends of the sponge 12. The free edge 52 of the distal portion 50 of the web 44 is enlarged, in the form of a rounded bulge.

As to the gripping members 46, they each are attached to the web 44 proximally via arms 56 and intermediately via supports 58. Each gripping member 46 also includes a proximal clamp-actuating section 60 and a distal sponge-clamping section 62. Each proximal clamp-actuating section 60 is attached to the web 44 proximally by a respective arm 56. The distal end of the clamp-actuating section 60 merges with the proximal end of the distal sponge-clamping section 62, and at this merging area the gripping member 46 is attached to the web 44 via the intermediate support 58. A groove 64 is defined in each intermediate support 58 to facilitate the flexing of the support 58, as described hereinafter.

Each proximal clamp-actuating section 60 includes a distal finger grip 66 provided with traction ribs 68, and also includes a proximal connecting portion 70 that link the finger grip 66 to the arm 56.

Each distal sponge-clamping section 62 is generally arcuate and includes a distal free clamping end 74 provided with an internal rib 76. The clamping ends 74 extend basically towards each other and towards ribs 54 of the distal portion 50 of the web 44, such as to hold the proximal ends of the sponge 12 securely between the clamping ends 74 and the web 44, as seen for instance in FIG. 10.

Figure 9:
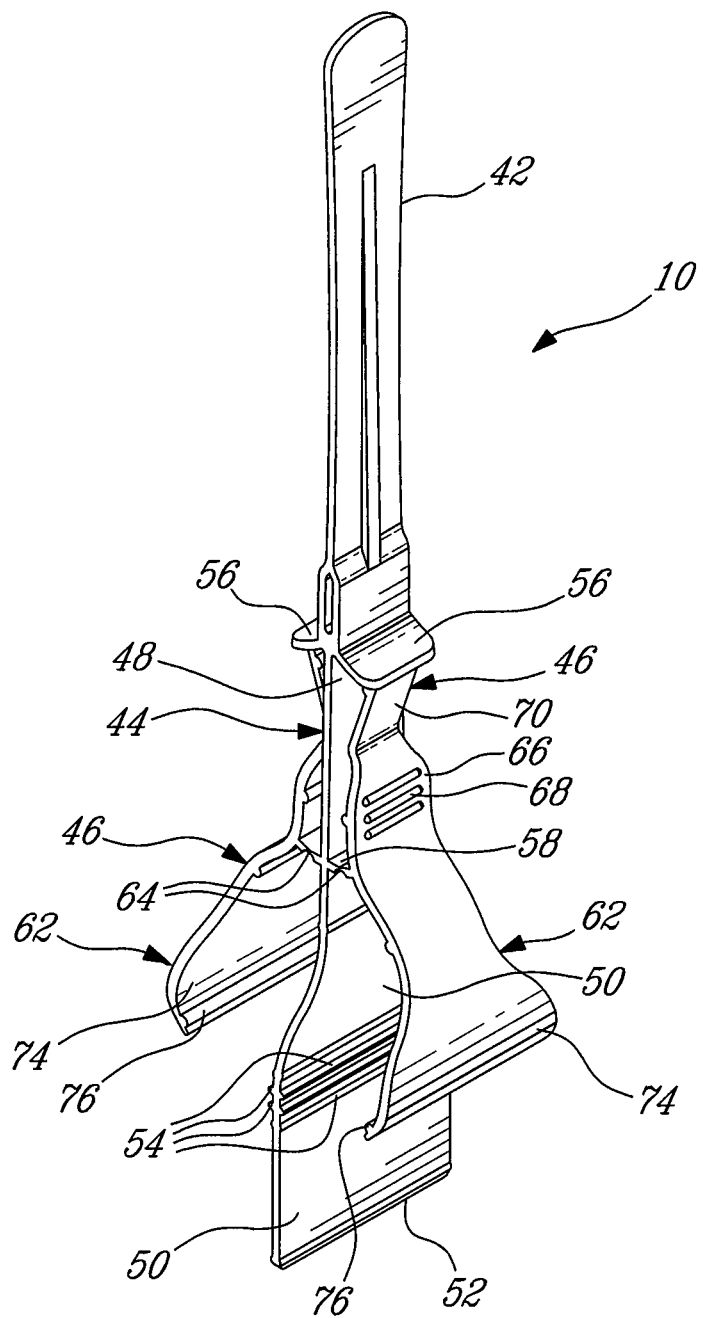
FIG. 9 is a perspective view of the handle of the sampling device, shown in a sponge-releasing position thereof.

The operation of the gripping members 46 will now be described. When depressed along arrows 72 (see FIG. 5b) by the user's fingers, the finger grips 66 move towards the proximal web portion 48, flexing occurring at the junctions of the finger grips 66 and connecting portions 70, and also at the junctions of the connecting portions 70 and the arms 56. The finger grips 66 are substantially rigidly connected to the clamping sections 62, whereby the internal movement of the finger grips 66 causes the clamping sections 62 to spread, i.e. move away from the web 44, as shown in FIG. 9. The combination of the finger grips 66 and the clamping sections 62 rock about the intermediate supports 58, which bend as needed via their inherent flexibility and/or their grooves 64. Once the finger grips 66 are released by the user, the various flexed portions of the gripping members 46 biasedly cause the gripping members 46 to return to their at rest sponge-clamping position shown in FIGS. 6 and 8.

Therefore, once the bag B has been opened (FIG. 3), the sampling device D is removed therefrom (using sterile gloves). The sampling device D is then displaced on the surface to be tested, such as surface S in FIG. 4 thereby causing the sponge 12 to swab the surface S and retrieve a sample therefrom. The bag B is then opened as in FIG. 5a, via pull tabs 40 and arrows 78. The gripping members 46 are then actuated via the finger grips 66 so as to spread the clamping sections 62 and release the sponge 12 into the bag B, as seen in FIG. 5b.

Figure 5C:
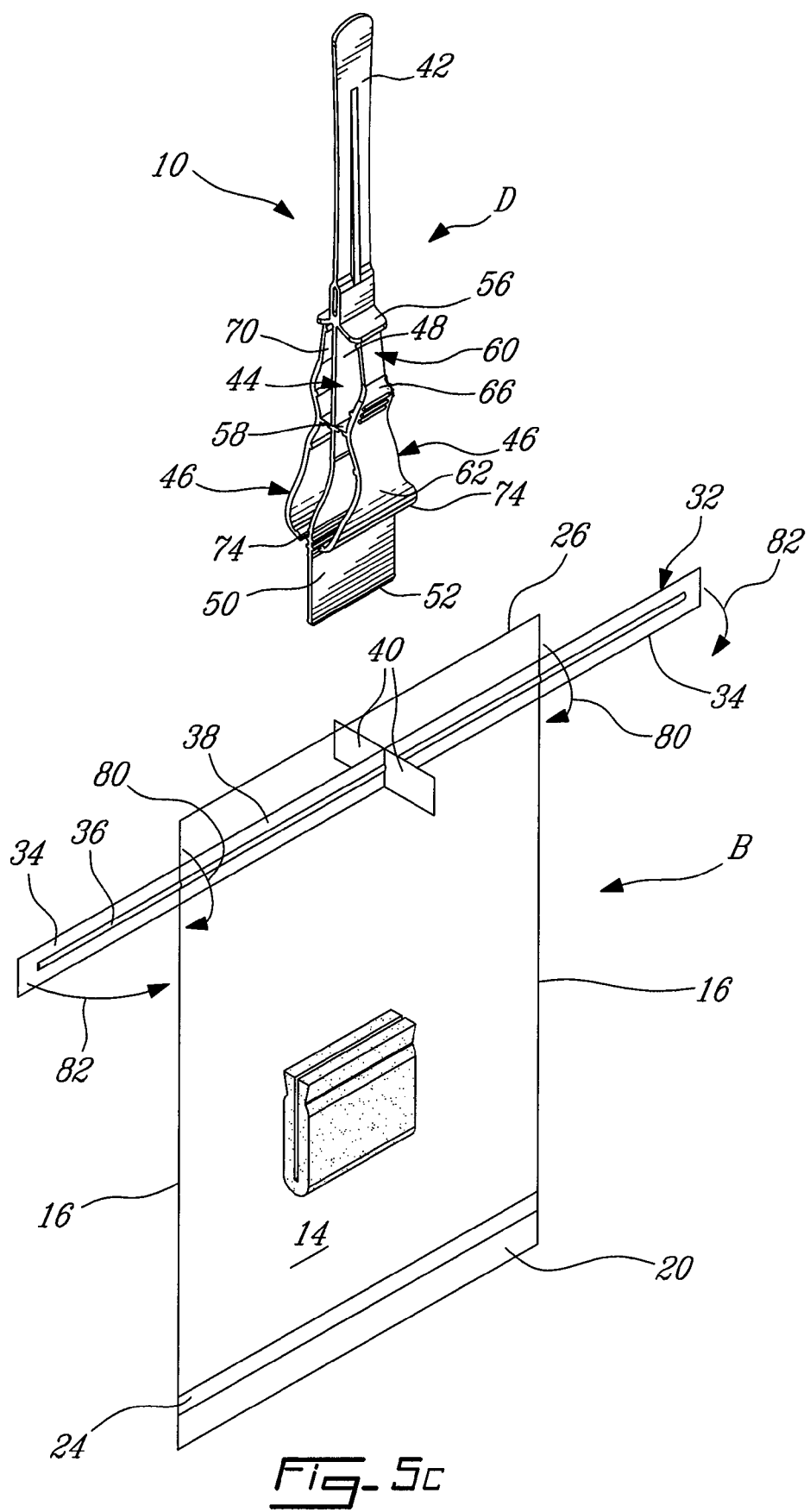
Figure 5D:
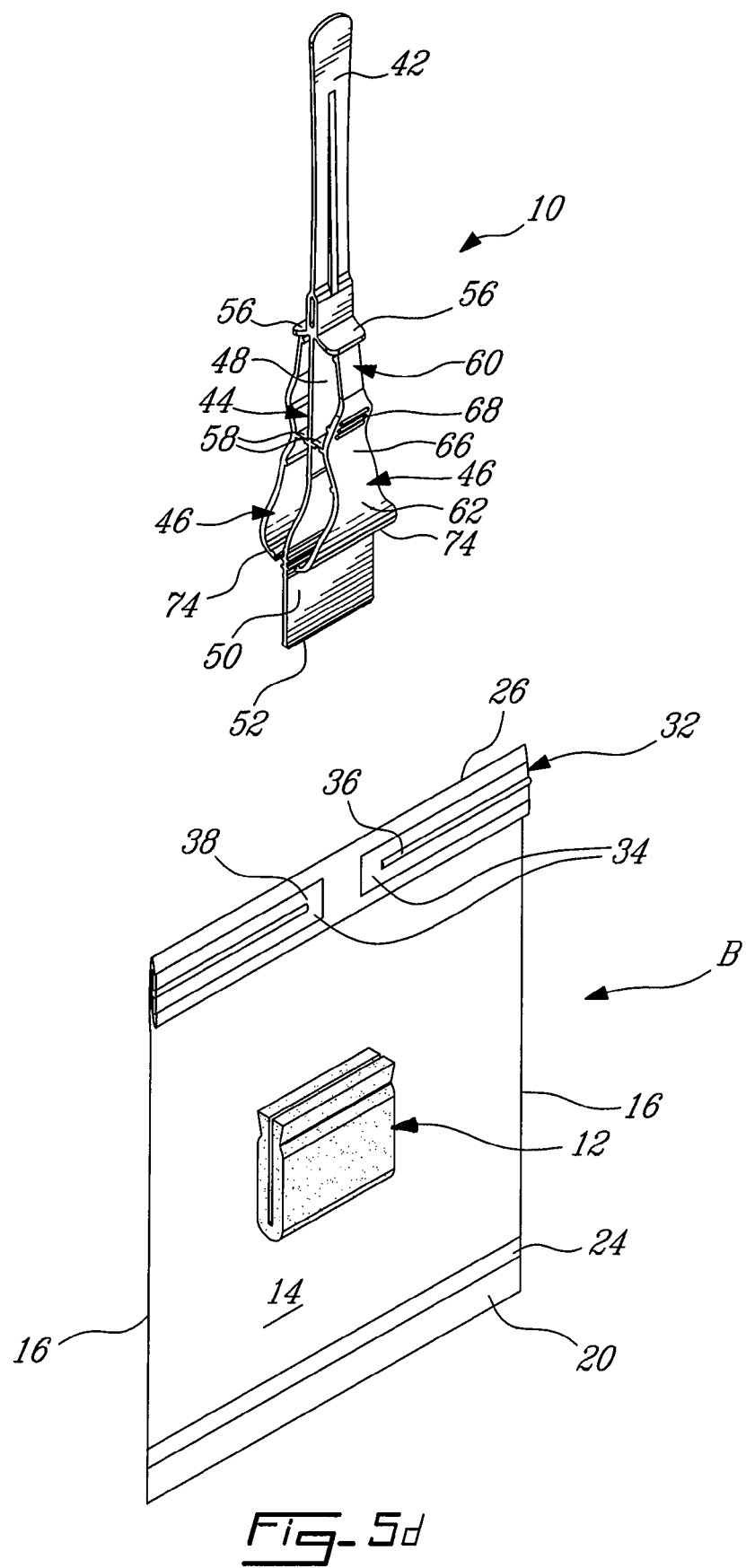
Figure 6:
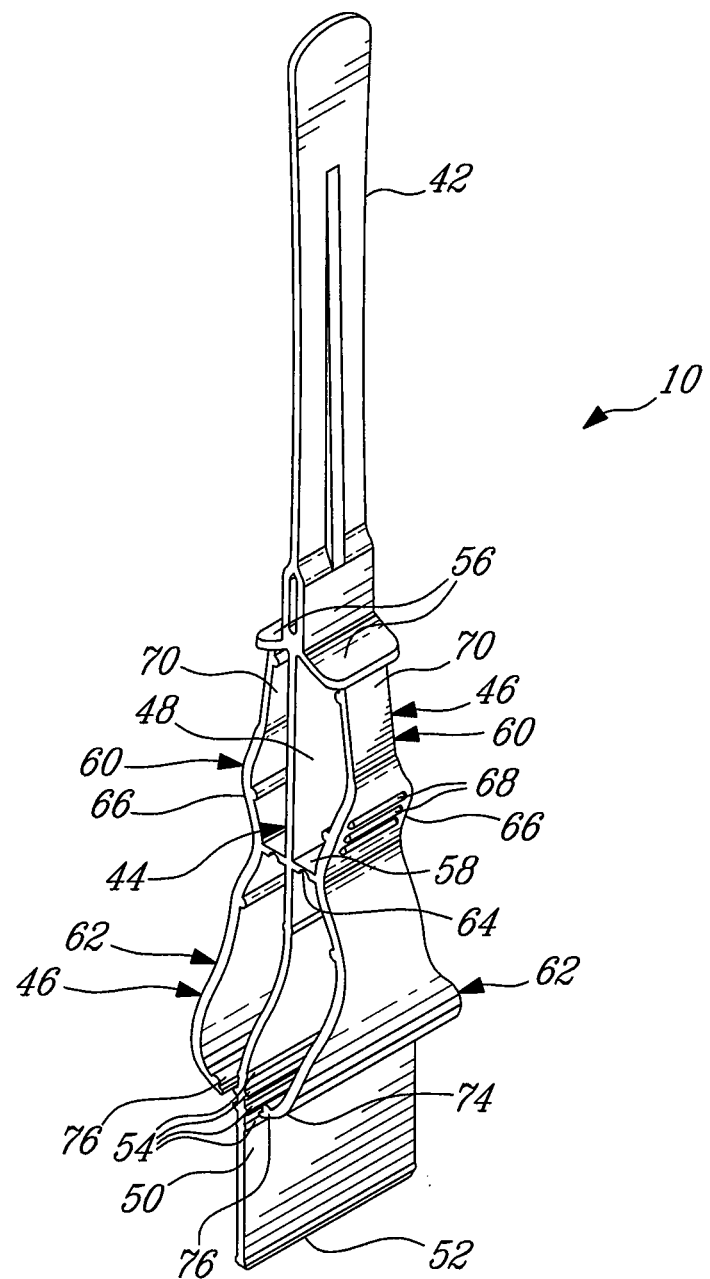
FIGS. 6 to 8 are respectively perspective, front elevation and side views of a handle of the sampling device, shown in a sponge-holding position thereof.
Figure 7:
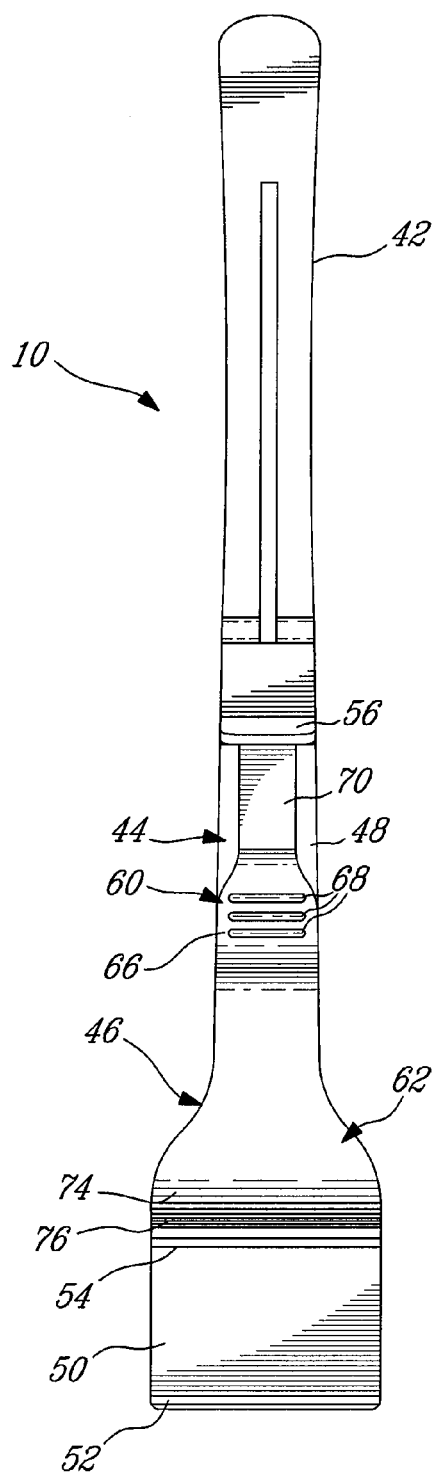
Figure 8:
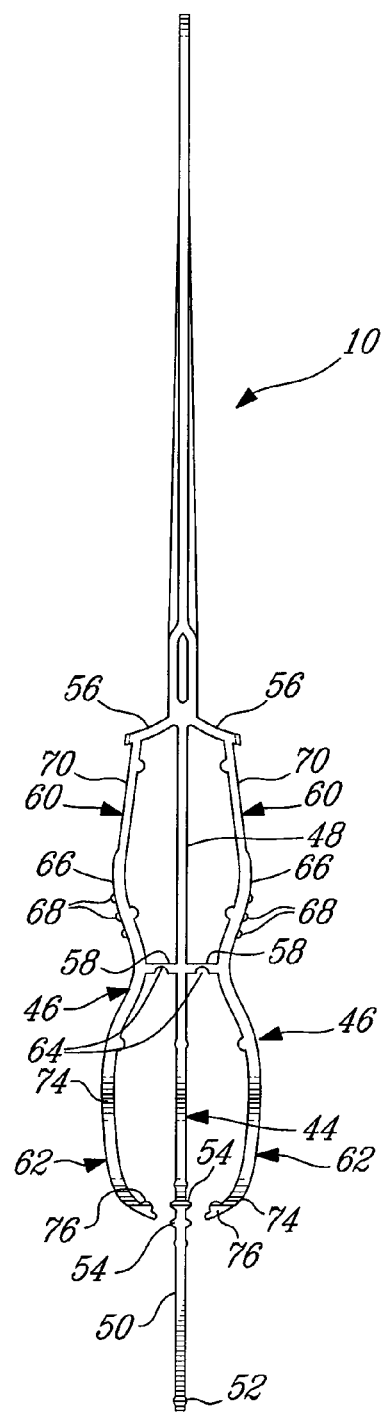

Referring to FIG. 5c, the bag B is then closed by first turning over the upper end 18 along arrows 80, and then the ends 34 of the closure members 32 are folded over the bag B along arrows 82. This seals the bag B with the swabbed sponge 12 therein, as seen in FIG. 5d.

It is noted that the sponge 12 located initially located in the bag B (FIG. 1) can be prehydrated with a given substance or can be dehydrated. The sponge 12 can typically have dimensions of 40 mm by 78 mm by 2 mm. The bag B can typically have dimensions of 4.5 inches by 9 inches.

The handle 10 can generally be reused, after proper sterilization, and the like. The handle can be made of suitable materials, such as polypropylene, lightweight, flexible HDPE-LDPE mix, etc.

There could be provided an extension adapted to be connected to the handle 10 so as to reach remote areas.

The handle 10 must generate sufficient pressure to retain the moist sponge 12 securely, yet have a release mechanism that is effective and can be operated with one hand, as seen hereinabove and in FIGS. 5a to 5c. Furthermore, in order to reduce complexity and cost, the design should consist of a single streamlined component. The design specifically enables a strong grip of the sponge 12 when not in use e.g. when in the bag B as in FIG. 1.

The design allows, through simple, one handed pressure on the thorax level (i.e. on finger grips 66) of the sampling device D, to release the sponge 12 in a controlled and efficient way.

The sampling device D is lightweight, and provides excellent grip on the moistened sponge 12. The release mechanism is integral to the design, is sufficiently robust and functions well, allowing the user to have a free hand to stabilize the bag B (or any other activity required).

Although the present invention has been described hereinabove by way of embodiments thereof, it may be modified, without departing from the nature and teachings of the subject invention as described herein.

The invention claimed is:

1. A kit for swabbing a surface and collecting a substance therefrom, comprising a device and a sampling bag, the device including a handle and a collecting member being releasably mounted to the handle, the handle and the collecting member mounted thereto being sealed in the sampling bag, the handle including an actuator and a pair of gripping members adapted to engage the collecting member and retain the collecting member mounted to the handle in a first position of the gripping members, wherein once the device has been removed from the sampling bag and the collecting member has been used to collect the substance from the surface, the gripping members are adapted, upon the actuator being appropriately displaced by fingers of a user, to be moved outwardly to a collecting member-release position thereof for releasing the collecting member from the handle and into the sampling bag, wherein the actuator is adapted to be displaced by the fingers of a given hand of the user transversally of a longitudinal axis of the handle to bring the gripping members to the collecting member-release position with the user holding the handle with the given hand as the user acts upon the actuator with the fingers of this same given hand.

2. A kit for swabbing a surface and collecting a substance therefrom, comprising a device and a sampling bag, the device including a handle and a collecting member being releasably mounted to the handle, the handle and the collecting member mounted thereto being sealed in the sampling bag, the handle including an actuator and a pair of gripping members adapted to engage the collecting member and retain the collecting member mounted to the handle in a first position of the gripping members, wherein once the device has been removed from the sampling bag and the collecting member has been used to collect the substance from the surface, the gripping members are adapted, upon the actuator being appropriately displaced by fingers of a user, to be moved outwardly to a collecting member-release position thereof for releasing the collecting member from the handle and into the sampling bag,
  wherein the actuator is provided proximally of the gripping members, wherein the gripping members are adapted, upon the actuator being displaced transversally of a longitudinal axis of the handle, to be moved outwardly to the collecting member-release position thereof for releasing the collecting member from the handle, and wherein pressure is exerted by the fingers of the user on the actuator such that each of the two gripping members is displaced,
  wherein there is provided one said actuator for each gripping member, and wherein the fingers of the user are adapted to exert pressure on both actuators to bring the two gripping members to the collecting member-release position without the user having to substantially move the fingers longitudinally along the handle,
  wherein the actuators are actuated transversally of the longitudinal axis of the handle to bring the gripping members to the collecting member-release position such that the user is not required to substantially move a given hand longitudinally along the handle to bring the gripping members from the first position to the collecting member-release position, and
  wherein the actuators are each displaced transversally towards the other by the fingers of the user so as to bring the gripping members to the collecting member-release position without requiring for the user to substantially move the given hand longitudinally along the handle.

3. The kit according to claim 1, wherein there is provided one said actuator for each gripping member, and wherein the fingers of the given hand of the user are adapted to exert pressure on both actuators to bring the pair of gripping members to the collecting member-release position without the user having to substantially move the fingers longitudinally along the handle.

4. The kit according to claim 3, wherein the actuators are actuated transversally of the longitudinal axis of the handle to bring the gripping members to the collecting member-release position such that the user is not required to substantially move the given hand longitudinally along the handle to bring the gripping members from the first position to the collecting member-release position.

5. The kit according to claim 4, wherein the actuators are each displaced transversally towards the other by the fingers so as to bring the gripping members to the collecting member-release position without requiring for the user to substantially move the given hand longitudinally along the handle.

6. The kit according to claim 3, wherein the pair of gripping members are opposed to each other, and wherein the pressure is exerted by the user's fingers on the actuator of each gripping member and towards one another.

7. The kit according to claim 3, wherein each gripping member includes a proximal actuating section and a distal clamping section, the proximal actuating section including the actuator and the distal clamping section being adapted to releasably hold the collecting member to the handle.

8. The kit according to claim 7, wherein the handle includes a hand grip and a web extending longitudinally therefrom, the gripping members extending on opposite sides of the web.

9. The kit according to claim 8, wherein proximal ends of the actuating sections are connected to at least one of the hand grip and the web, wherein distal ends of the actuating sections are connected to proximal ends of the clamping sections, and wherein distal ends of the clamping sections are adapted in the first position to engage the collecting member therebetween.

10. The kit according to claim 9, wherein for each gripping member a support is provided, each support extending from the web to a connection area of the distal end of a respective actuating section with a proximal end of the clamping section associated thereto.

11. The kit according to claim 10, wherein the gripping members are adapted to pivot about the supports when actuated between the first position and the collecting member-release position.

12. The kit according to claim 11, wherein the actuating sections are adapted to flex inwardly when depressed by the user, thereby causing the gripping members to pivot about the supports and the distal ends of the clamping sections to spread away from the web to the collecting member-release position, thereby releasing the collecting member from the handle.

13. The kit according to claim 12, wherein the web extends distally past the distal ends of the clamping sections such that the collecting member, in a folded position thereof, has a fold thereof located at a distal free edge of the web, the collecting member extending rearwardly from the distal free edge on each side of the web such that the proximal ends of the collecting member are held to the web by the distal ends of the clamping sections.

14. The kit according to claim 9, wherein the collecting member is adapted to be positioned along at least one side of a distal end of the web, with the distal ends of the clamping sections being adapted to exert inward pressure on the collecting member such that the collecting member is held by the clamping sections on the web.

15. The kit according to claim 1, wherein the collecting member includes a sponge.

\* \* \* \* \*